United States Patent
Liaw

(10) Patent No.: US 7,282,553 B2
(45) Date of Patent: Oct. 16, 2007

(54) FLEXIBLE ISOPROPYLIDENE AND TETRAMETHYL-CONTAINING FLUOROPOLYAMIDE AND FLUOROPOLYMIDE AND PREPARATION METHOD THEREOF

(75) Inventor: Der-Jang Liaw, Taipei (TW)

(73) Assignee: National Taiwan University of Science & Technology, Taipei (TW)

( * ) Notice: Subject to any disclaimer, the term of this patent is extended or adjusted under 35 U.S.C. 154(b) by 484 days.

(21) Appl. No.: 10/883,117

(22) Filed: Jun. 30, 2004

(65) Prior Publication Data

US 2005/0101756 A1    May 12, 2005

(30) Foreign Application Priority Data

Nov. 11, 2003  (TW) .............................. 92131604 A

(51) Int. Cl.
*C07C 205/38* (2006.01)
(52) U.S. Cl. ...................... 528/170; 528/162; 528/168; 528/124; 528/123
(58) Field of Classification Search ................ 528/162, 528/168, 124, 123
See application file for complete search history.

(56) References Cited

U.S. PATENT DOCUMENTS 6,087,470 A * 7/2000 Liaw et al. .................. 528/310

OTHER PUBLICATIONS

Chin-Ping Yang et al Organosoluble and optically transparent polyimides . . . Polymer43 (2002) 5095-5104.*
Liaw et al Highly organosoluble . . . Journal of Pol Sci, Part A vol. 42, p. 5766-5774.*

* cited by examiner

*Primary Examiner*—James J. Seidleck
*Assistant Examiner*—Gregory Listvoyb

(57) ABSTRACT

Polyamides and polyimides containing flexible isopropylidene, trifluoromethyl and tetramethyl substituents and their synthetic method are disclosed. Polyamide containing flexible isopropylidene, trifluoromethyl and tetramethyl substituents is synthesized by reacting diamine compound (2,2-bis[4-(2-trifluoromethyl-4-aminophenoxy)-3,5-dimethylphenyl]propane) with an equimolar diacid via a polycondensation reaction. Polyimide containing flexible isopropylidene, trifluoromethyl and tetramethyl substituents is synthesized by reacting diamine compound with an equimolar dianhydride via a polycondensation reaction. The novel polyamide and polyimide containing flexible isopropylidene, trifluoromethyl and tetramethyl substituents are synthesized from the diamine compound containing flexible isopropylidene, trifluoromethyl and tetramethyl substituents, wherein the polyamides and polyimides containing flexible isopropylidene, trifluoromethyl and tetramethyl substituents have appropriate thermal stability, mechanical properties, and processability.

13 Claims, No Drawings

FLEXIBLE ISOPROPYLIDENE AND TETRAMETHYL-CONTAINING FLUOROPOLYAMIDE AND FLUOROPOLYMIDE AND PREPARATION METHOD THEREOF

FIELD OF THE INVENTION

This invention relates to the synthetic methods of polyamides and polyimides containing flexible isopropylidene, trifluoromethyl and tetramethyl substituents with appropriate thermal stability and mechanical properties.

BACKGROUND OF THE INVENTION

Polyamides and polyimides are important engineering plastics. Since these kinds of plastic materials have excellent mechanical properties and thermal stability, they have been applied widely in the semiconductor industry, photoelectric industry, aviation industry, biomedical material industry, automobile industry, communication material industry, engineering industry and thin-film manufacturing industry. However, since the polyimide, which has excellent electrical property, is also applied in the basal material of the semiconductor and the packing substance, it becomes one of the most important materials for the high-technology industry.

Polyamides and polyimides are hard to be processed due to their high softening temperature, so they cannot be processed via the heating method. On the other hand, polyamides and polyimides with poor solubility can hardly be dissolved in organic solvents for easy processing. Therefore, most of the polyamides and polyimides are difficult to process.

Taking Kevlar as an example, which is a commercial product produced by DuPont Corporation US, since it could only be dissolved in the high polar solvents; the processing method for Kevlar is limited. It is inconvenient to process most kinds of the polyimides. For example, Kapton produced by DuPont Corporation US, which has a high softening temperature, is synthesized via a two-step method including the thin film manufacturing method and the wire coating method. The thin film, which is the precursor of polyimide formed by casting the poly(amic acid) solution, is formed as the membrane of polyimide after cyclodehydration procedure. Kapton is hard to be processed due to a high softening temperature and poor solubility (only soluble in concentrated sulfuric acid). In order to increase the processability and the application field of the polymers, solubility is very important issue preparation of polyamides and polyimides with better solubility becomes important.

Therefore, the present invention provides the synthetic methods for preparing the polyamides and polyimides with better physical and chemical properties (excellent solubility, lower dielectric constant, excellent thermal stability, excellent mechanical properties excellent processability, excellent optical property and decreasing water absorption) so as to overcome the drawbacks of the prior art described above.

SUMMARY OF THE INVENTION

It is an aspect of the present invention to provide an easier preparing method for the polyamide and polyimide containing flexible isopropylidene, trifluoromethyl and tetramethyl substituents with excellent thermal stability, mechanical properties and processability so as to overcome the drawbacks of the common engineering plastics and increase the application fields and the relevant value added.

Another aspect of the present invention is to provide a polyamide containing flexible isopropylidene, trifluoromethyl and tetramethyl substituents generated from a diamine compound containing flexible isopropylidene, trifluoromethyl and tetramethyl substituents and an equimolar diacid via a polycondensation reaction, and a polyimide containing flexible isopropylidene, trifluoromethyl and tetramethyl substituents generated from a diamine compound containing flexible isopropylidene, trifluoromethyl and tetramethyl substituents and an equimolar dianhydride compound via a polycondensation reaction.

The further aspect of the present invention is to provide novel polyamide and polyimide containing flexible isopropylidene, trifluoromethyl and tetramethyl substituents which are synthesized from the diamine compound containing flexible isopropylidene, trifluoromethyl and tetramethyl substituents.

In accordance with an aspect of the present invention, the preparing method is provided to synthesize the diamine compound, which contains flexible isopropylidene, trifluoromethyl and tetramethyl substituents. The polymer containing flexible isopropylidene, trifluoromethyl and tetramethyl substituents has the following characteristics: (1) excellent solubility (2) lower dielectric constant (3) excellent thermal stability (4) excellent mechanical properties (5) excellent processability (6) excellent optical property and (7) decreasing water absorption. The diamine compound containing tetramethyl substituents has the following characteristic: (1) better solubility and (2) decreasing the intramolecular force (the tetramethyl substituents, forming a stereo-hindrance to block the rigidly stacking of the molecule, reducing the crystallinity and increasing the solubility). The engineering plastic materials of the polyamide and polyimide containing flexible isopropylidene, trifluoromethyl and tetramethyl substituents synthesized from the diamine compound are expected to have an excellent thermal stability, mechanical properties and easier processability. With the specific structure, it is easy to make a thin film to be the separation material applied for the gas separation.

In accordance with another aspect of the present invention, the method is provided for preparing a dinitro compound containing flexible isopropylidene, trifluoromethyl and tetramethyl substituents (I), wherein the structure of the dinitro compound (I) is shown as following:

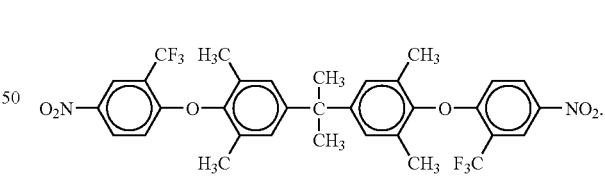

I

The dinitro compound containing flexible isopropylidene, trifluoromethyl and tetramethyl substituents (I) is obtained by performing a reaction of 2,2-bis-(4-hydroxy-3,5-dimethylphenyl)propane and 2-chloro-5-nitrobenzotrifluoride.

Preferably, the reaction carried out in presence of the potassium carbonate ($K_2CO_3$).

Preferably, the N,N-dimethylformamide (DMF) is used as a solvent in the reaction.

Preferably, the reaction is performed at the refluxing temperature.

Preferably, after being cooled down to the ambient temperature, the reaction mixture is poured into methanol-water to obtain a precipitated compound.

Preferably, the precipitated compound is purified and recrystallized from glacial acetic acid.

In accordance with another aspect of the present invention, a method is provided for preparing a diamine compound containing flexible isopropylidene, trifluoromethyl and tetramethyl substituents (II), wherein the structure of the diamine (II) is showed as following:

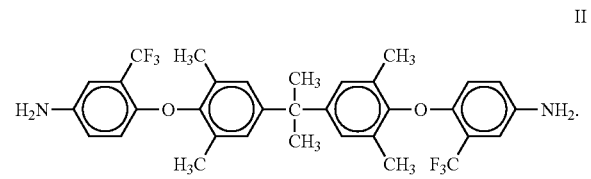

II

It includes steps of (a) carrying out the reaction in solution which contains the dinitro compound containing flexible isopropylidene, trifluoromethyl and tetramethyl substituents (I) and an ethanol solvent, (b) heating the reaction solution to the refluxing temperature, and (c) adding the hydrazine monohydrate into the reaction solution slowly, and a obtaining diamine compound after filtration of the reaction mixture.

Preferably, the 10% palladium/activated carbon is used as the catalyst.

Preferably, the reaction is performed under refluxing condition.

Preferably, the 10% palladium/activated carbon is filtrated out of the reaction solution, and the solution is cooled down into the ambient temperature.

Preferably, the obtaining compound is purified and recrystallized from ethanol.

In accordance with another aspect of the present invention, a method is provided for preparing a polyamide containing flexible isopropylidene, trifluoromethyl and tetramethyl substituents (III), wherein the structure of the polyamide (III) is shown as following:

Wherein $Ar_1$ is one selected from a group consisting of:

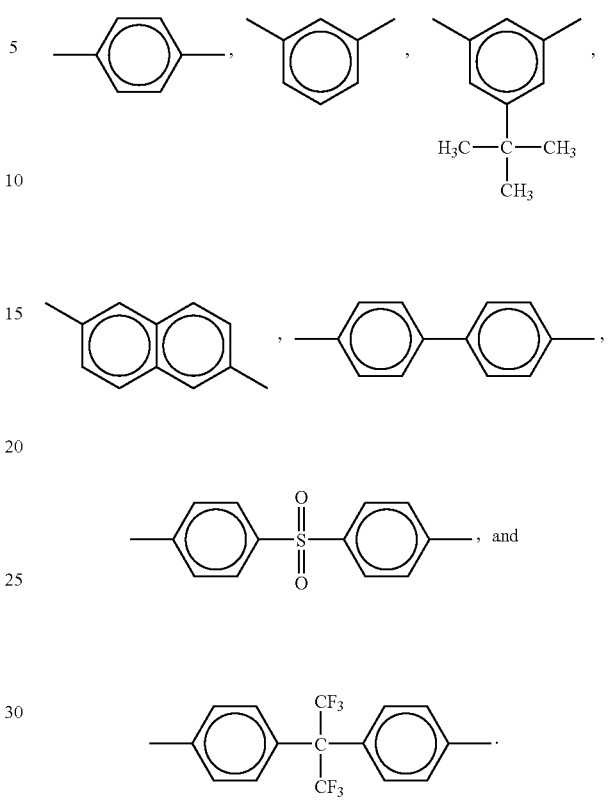

The method includes performing a reaction of the diamine compound containing flexible isopropylidene, trifluoromethyl and tetramethyl substituents (II) and equimolar diacid to obtain the polyamide containing flexible isopropylidene, trifluoromethyl and tetramethyl substituents (III).

Preferably, the reaction solution contains calcium chloride ($CaCl_2$), triphenyl phosphite (TPP), pyridine, and N-methyl-2-pyrrolidinone (NMP).

In accordance with another aspect of the present invention, a method is provided for preparing a polyimide containing flexible isopropylidene, trifluoromethyl and tetramethyl substituents (IV), wherein the structure of the polyimide (IV) is shown as following:

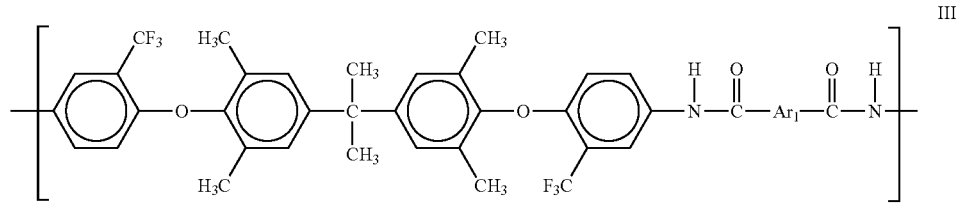

III

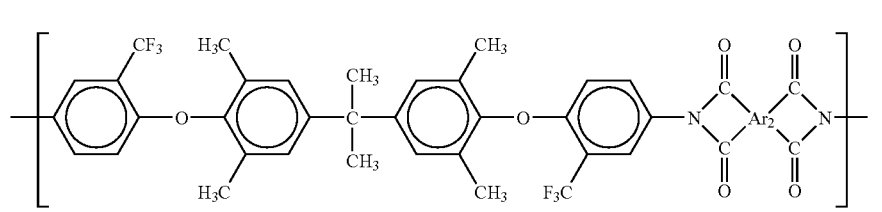

Wherein Ar$_2$ is one selected from a group consisting of:

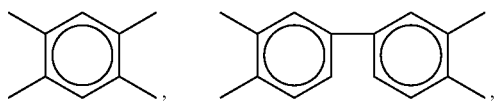

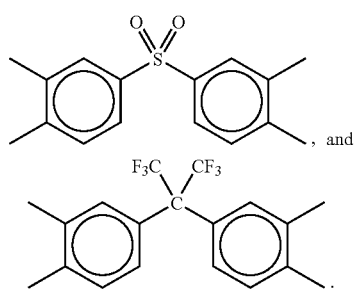

The method includes performing a reaction of the diamine compound containing flexible isopropylidene, trifluoromethyl and tetramethyl substituents (II) and equimolar dianhydride to obtain the polyimide containing flexible isopropylidene, trifluoromethyl and tetramethyl substituents (IV).

Preferably, the method uses N,N-dimethylacetamide (DMAc) as a solvent in the reaction.

Preferably, the reaction solution further stirred at ambient temperature for 2-4 hrs under argon atmosphere to form the poly(amic acid) solution.

Preferably, a mixture of acetic anhydride and pyridine is added in the reaction solution.

Preferably, the reaction is performed to obtain the polyimide containing flexible isopropylidene, trifluoromethyl and tetramethyl substituents at a refluxing temperature after the cyclodehydration.

DETAILED DESCRIPTION OF THE PREFERRED EMBODIMENT

The invention describes more specifically with reference to the following embodiments. It is to be noted that the following descriptions of preferred embodiments of this invention are presented herein for the purpose of illustration and description only; it is not intended to be exhaustive or to be limited to the precise form disclosed.

Embodiment I

Synthesis of Dinitro Compound Containing Flexible Isopropylidene, Trifluoromethyl and Tetramethyl Substituents of 2,2-bis [4-(2-trifluoromethyl-4-nitrophenoxy)-3,5-dimethylphenyl]-propane (I).

The reaction is performed by mixing the diol (A), 2,2-bis(4-hydroxy-3,5-dimethylphenyl)propane 8.00 gram (28 mmol), 2-chloro-5-nitrobenzotrifluoride (B) 12.71 gram (56 mmol), potassium carbonate 9.80 gram, and N,N-dimethylformamide (DMF) 55 mL and refluxing for 8 hrs. The reaction mixture is cooled to ambient temperature and poured into methanol-water mixture (1:1 by volume). The crude product is recrystallized from glacial acetic acid to provide brown needles (m.p. 205° C. by DSC) in 88% yield. The IR spectrum (KBr) exhibited absorption bands at 1520 and 1333 cm$^{-1}$ (NO$_2$), 1259 cm$^{-1}$ (C—O—C). The relevant NMR analyses are:

$^1$HNMR(CDCl$_3$): δ (ppm)=1.74 (s, 6H), 2.12 (s, 12H), 6.67 (d, J=9.15 Hz, 2H), 7.06 (s, 4H), 8.29 (dd, J=9.15, 2.10 Hz, 2H), 8.61 (s, J=2.10 Hz, 2H)。

$^{13}$C NMR (CDCl$_3$): δ(ppm)=16.16, 30.87, 42.28, 113.90, 118.53, 118.79, 119.05, 119.32 (quartet, $^2J_{C-F}$=33.12 Hz), 119.11, 121.29, 123.46, 125.63 (quartet, $^1J_{C-F}$=273.34 Hz), 124.01, 124.05 (doublet, $^3J_{C-F}$=5.03 Hz), 127.85, 129.08, 129.94, 141.16, 147.39, 148.67, 160.30。

The elemental analysis is: Calculated value: C, 59.82%; H, 4.26%; N, 4.23% Observed value: C, 60.19%; H, 4.34%; N, 4.16%

The reaction scheme is outlined as following:

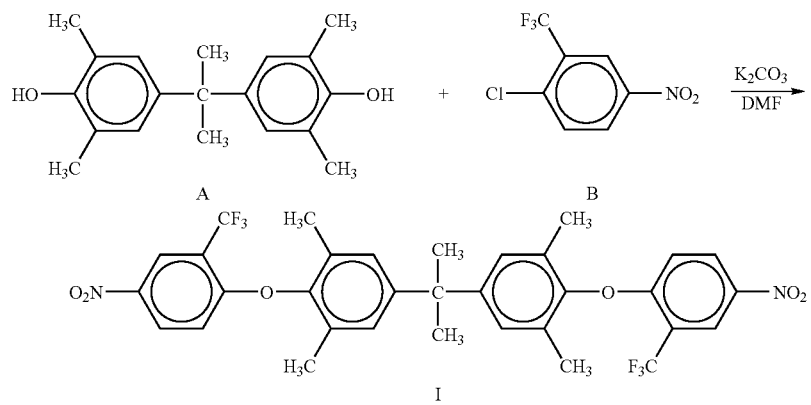

Embodiment II

Synthesis of the Diamine Compound Containing Flexible Isopropylidene, Trifluoromethyl and Tetramethyl Substituents 2,2-bis [4-(2-trifluoromethyl-4-aminophenoxy)-3,5-dimethylphenyl]-propane (II).

The reaction is performed by mixing of 12.48 gram (19 mmol) 2,2-bis[4-(2-trifluoromethyl-4-nitrophenoxy)-3,5-dimethylphenyl]propane, 0.12 gram 10% Pd/C and 40 mL ethanol and the mixture is placed in a three-necked flask. 6 mL hydrazine monohydrate is added dropwise over a period of 0.5 hr at 95° C. After the completion of addition, the reaction refluxed at 95° C. for another 24 hrs. The reaction mixture is then filtered to remove Pd/C. After cooling, the monomer is isolated by filtration, recrystallized from ethanol and dried under vacuum. The yield is 72%; m.p. 212° C. by DSC. The IR spectrum (KBr) exhibited absorption bands at 3444 and 3368 $cm^{-1}$ due to N—H bond, 1225 $cm^{-1}$ due to C—O—C. The relevant NMR analyses are:

$^1$H NMR (DMSO-$d_6$): δ (ppm)=1.64 (s, 6H), 2.01 (s, 12H), 5.10 (s, 4H), 6.15 (d, J=8.85 Hz, 2H), 6.65 (dd, J=8.85, 2.28 Hz, 2H), 6.96 (s, J=2.28 Hz, 2H), 7.02 (s, 4H)。

$^{13}$C NMR (DMSO-$d_6$): δ (ppm)=15.94, 30.60, 41.64, 111.94, 111.98 (doublet, $^3J_{C-F}$=5.03 Hz), 113.88, 116.16, 116.40, 116.64, 116.88 (quartet, $^2J_{C-F}$=30.18 Hz), 118.57, 120.79, 122.96, 125.12, 127.29 (quartet, $^1J_{C-F}$=272.50 Hz), 127.23, 129.94, 142.93, 145.47, 147.10, 147.98。

The elemental analysis is: Calculated value C, 65.77%; H, 5.35%; N, 4.65% Observed value: C, 65.86%; H, 5.16%; N, 4.52%

The reaction scheme is outlined as following

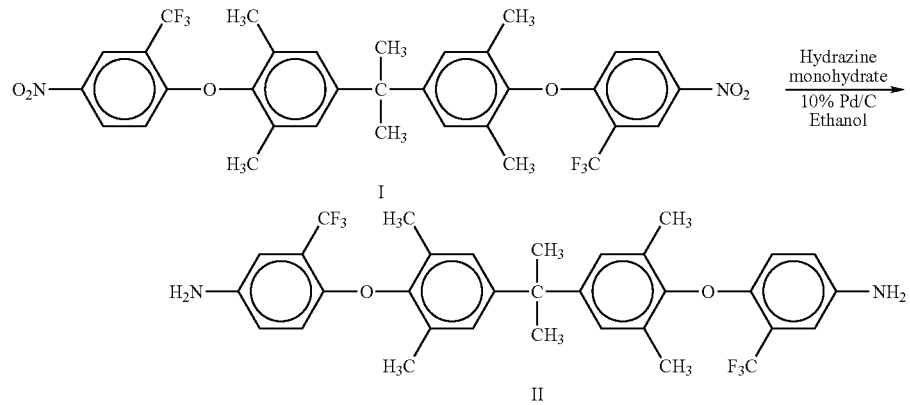

Embodiment III

Synthesis of the Novel Polyamide Containing Flexible Isopropylidene Trifluoromethyl and Tetramethyl Substituents from 2,2-bis[4-(2-trifluoromethyl-4-aminophenoxy)-3,5-dimethylphenyl]-propane and Terephthalic Acid The polymerization reaction is preformed by polycondensation method. A mixture of 1 mmole of diamine (II), 2,2-bis[4-(2-trifluoromethyl-4-aminophenoxy)-3,5-dimethylphenyl]-propane, 1 mmole of terephthalic acid (C), 0.35 gram of calcium chloride ($CaCl_2$), 0.9 mL of triphenyl phosphite (TPP), 0.9 mL of pyridine, and 5 mL of N-methyl-2-pyrrolidinone (NMP) is heated with stirring at 130 □ for 3 hrs under argon flowing condition. As the reaction proceeded, the solution gradually became highly viscous. After cooling, the polymer is precipitated by pouring the reaction mixture into a large quantity of methanol with constant stirring. The precipitate is washed thoroughly with methanol and hot water, filtered, and dry at 100° C. under vacuum for 24 hrs. The inherent viscosity of the polymer in N,N-dimethylacetamide (DMAc) is 0.78 dL·g$^{-1}$, measured at a concentration of 0.5 g·dL$^{-1}$ at 30° C. The IR spectrum of polyamide which exhibited absorption bands at 3418 and 3303 cm$^{-1}$ ($v_{N-H}$), 1233 cm$^{-1}$ ($v_{C-O-C}$). The polyamide possesses outstanding film-forming properties. Highly transparent flexible film is obtained by casting polymer solution in N,N-dimethylacetamide (DMAc) onto glass plates, following by gradually heating up to 150° C. under vacuum to remove the solvent.

TABLE 1

Characterization of the properties of the polyamide containing flexible isopropylidene, trifluoromethyl and tetramethyl substituents in embodiment III

| | |
|---|---|
| Mechanical properties of thin film | Tensile strength: 83 MPa; Elongation at break: 6%; Tensile modulus: 1.7 GPa o |
| Solubility | The polymer can be dissolved in N-methyl-2-pyrrolidinone (NMP), N,N-dimethylacetamide (DMAc), N,N-dimethylformamide (DMF), dimethyl sulfoxide (DMSO), pyridine and tetrahydrofuran (THF), etc. |
| Thermal properties | Glass transition temperature: 243° C.; 10% weight loss temperature in the air: 475° C.; 10% weight loss temperature in the nitrogen: 464° C.. |
| Dielectric constant | 3.78 (1 KHz) |
| Elemental analysis | Calculated value: C, 67.21%; H, 4.68%; N, 3.82% Observed value: C, 66.27%; H, 4.67%; N, 3.77% |

The reaction scheme is outlined as following:

Embodiment IV

Synthesis of the Novel Polyamide Containing Flexible Isopropylidene, Trifluoromethyl and Tetramethyl Substituents from 2,2-bis[4-(2-trifluoromethyl-4-aminophenoxy)-3,5-dimethylphenyl]-propane and 4,4'-biphenyldicarboxylic Acid The polymerization reaction is performed by polycondensation method. A mixture of 1 mmole of diamine (II), 2,2-bis[4-(2-trifluoromethyl-4-aminophenoxy)-3,5-dimethylphenyl]-propane, 1 mmole of 4,4'-biphenyldicarboxylic acid (D), 0.35 gram of calcium chloride (CaCl$_2$), 0.9 mL of triphenyl phosphite (TPP), 0.9 mL of pyridine, and 5 mL of N-methyl-2-pyrrolidinone (NMP) is heated with stirring at 130° C. for 3 hrs under argon flowing condition. As the reaction proceeded, the solution gradually became highly viscous. After cooling, the polymer is precipitated by pouring the reaction mixture into a large quantity of methanol with constant stirring. The precipitate is washed thoroughly with methanol and hot water, filtered, and dry at 100 □ under vacuum for 24 hrs. The viscosity of the polyamide in N,N-dimethylacetamide (DMAc) is 0.65 dL·g$^{-1}$ (the concentration of the solution is 0.5 g·dL$^{-1}$, the measuring temperature is 30° C.). The IR spectrum of polyamide which exhibited absorption bands at 1675 cm$^{-1}$ (C=O). Highly transparent flexible film is obtained by casting polymer solution in N,N-dimethylacetamide (DMAc) onto glass plates, following by gradually heating up to 150° C. under vacuum to remove the solvent.

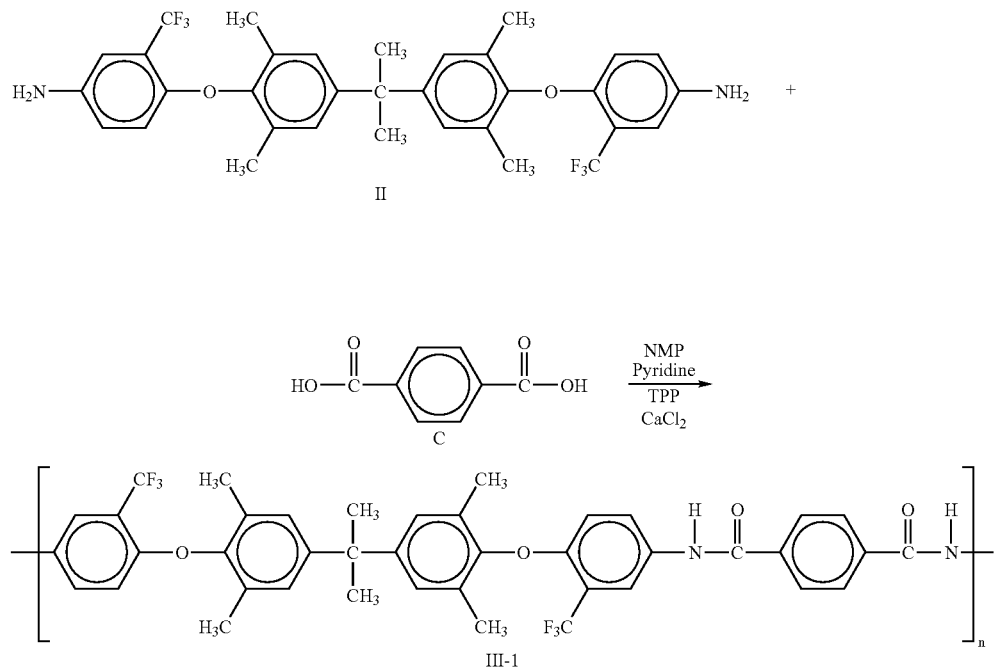

III-1

TABLE 2

Characterization of the polyamide containing flexible isopropylidene, trifluoromethyl and tetramethyl substituents in embodiment IV

| | |
|---|---|
| Mechanical properties of thin film | Tensile strength: 81 MPa; Elongation at break: 7%; Tensile modulus: 2.3 GPa o |
| Solubility | The polymer can be dissolved in N-methyl-2-pyrrolidinone (NMP), N,N-dimethylacetamide (DMAc), N,N-dimethylformamide (DMF), dimethyl sulfoxide (DMSO), pyridine and tetrahydrofuran (THF), etc. |
| Thermal properties | Glass transition temperature: 283° C.; 10% weight loss temperature in the air: 479° C.; 10% weight loss temperature in the nitrogen: 478° C.. |
| Dielectric constant | 3.71 (1 KHz) |
| Elemental analysis | Calculated value: C, 69.80%; H, 4.74%; N, 3.46% Observed value: C, 69.04%: H, 4.69%: N, 3.49% |

The reaction scheme is outlined as following

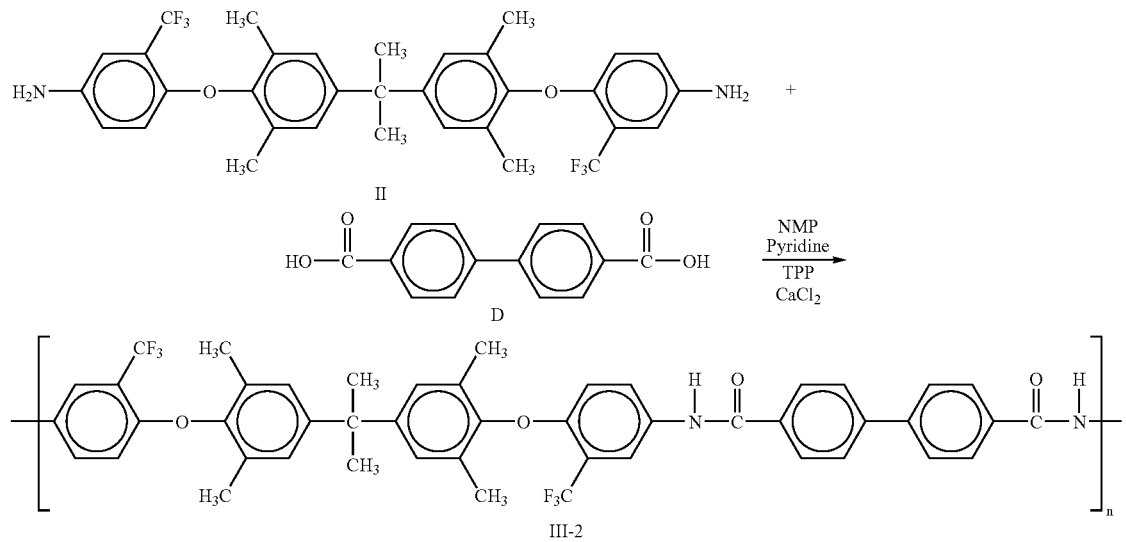

Embodiment V

Synthesis of the Novel Polyimide Containing Flexible Isopropylidene Trifluoromethyl and Tetramethyl Substituents from 2,2-bis [4-(2-trifluoromethyl-4-aminophenoxy)-3,5-dimethylphenyl]-propane with the Pyromellitic Dianhydride The reaction is performed by mixing a stirred solution of 1 mmol of 2,2-bis[4-(2-trifluoromethyl-4-aminophenoxy)-3,5-dimethylphenyl]propane (II) in 3.5 mL of N,N-dimethylacetamide (DMAc), 1 mmol of pyromellitic dianhydride (E) are gradually added. The mixture is stirred at ambient temperature for 2-4 hrs under argon atmosphere to form the poly(amic acid). Chemical cyclodehydration is carried out by adding 0.6 mL of acetic anhydride and 0.6 mL of pyridine into the above-mentioned poly(amic acid) solution with stirring at ambient temperature for an hr, and then heating at 110° C. for 3 hrs. The polymer solution is poured into methanol. The precipitate is filtered, washed thoroughly with methanol and hot water, and dried at 100° C. under vacuum. The inherent viscosity of the polymer in N,N-dimethylacetamide (DMAc) is 0.58 dL·g$^{-1}$, measured at a concentration of 0.5 g·dL$^{-1}$ at 30° C. The IR spectrum (film) of the polyimide exhibited absorption bands at 1778 and 1723 cm$^{-1}$, which are attributed to the asymmetric and symmetric stretches of imide carbonyl groups, respectively. The C—N stretching absorption band at 1374 cm$^{-1}$ confirmed the formation of imide structure. Highly transparent flexible film is obtained by casting polymer solution in N,N-dimethylacetamide (DMAc) onto glass plates, following by gradually heating up to 150° C. under vacuum to remove the solvent.

TABLE 3

Characterization of the polyimide containing flexible isopropylidene, trifluoromethyl and tetramethyl substituents in embodiment V

| | |
|---|---|
| Molecular weight | Number average molecular weights: 2.0 × 10$^4$ PDI: 2.89 |
| | Number of repeating unit: 25 |
| Mechanical properties of thin film | Tensile strength: 87 MPa; Elongation at break: 7%; Tensile modulus: 2.2 GPa o |
| Solubility | The polymer can be dissolved in N-methyl-2-pyrrolidinone (NMP), N,N-dimethylacetamide (DMAc), N,N-dimethylformamide (DMF), chloroform, pyridine and tetrahydrofuran (THF), etc. |
| Thermal properties | Glass transition temperature: 307° C.; 10% weight loss temperature in the air: 427° C.; 10% weight loss temperature in the nitrogen: 457° C.. |
| Dielectric constant | 3.00 (1 KHz) |
| Optical properties | Wavelength of transmittance 80%: 496 nm Cut-off wavelength: 394 nm |
| Elemental analysis | Calculated value: C, 65.82%; H, 3.85%; N, 3.57% Observed value: C, 65.21%; H, 3.90%; N, 3.17% |

The reaction scheme is outlined as following:

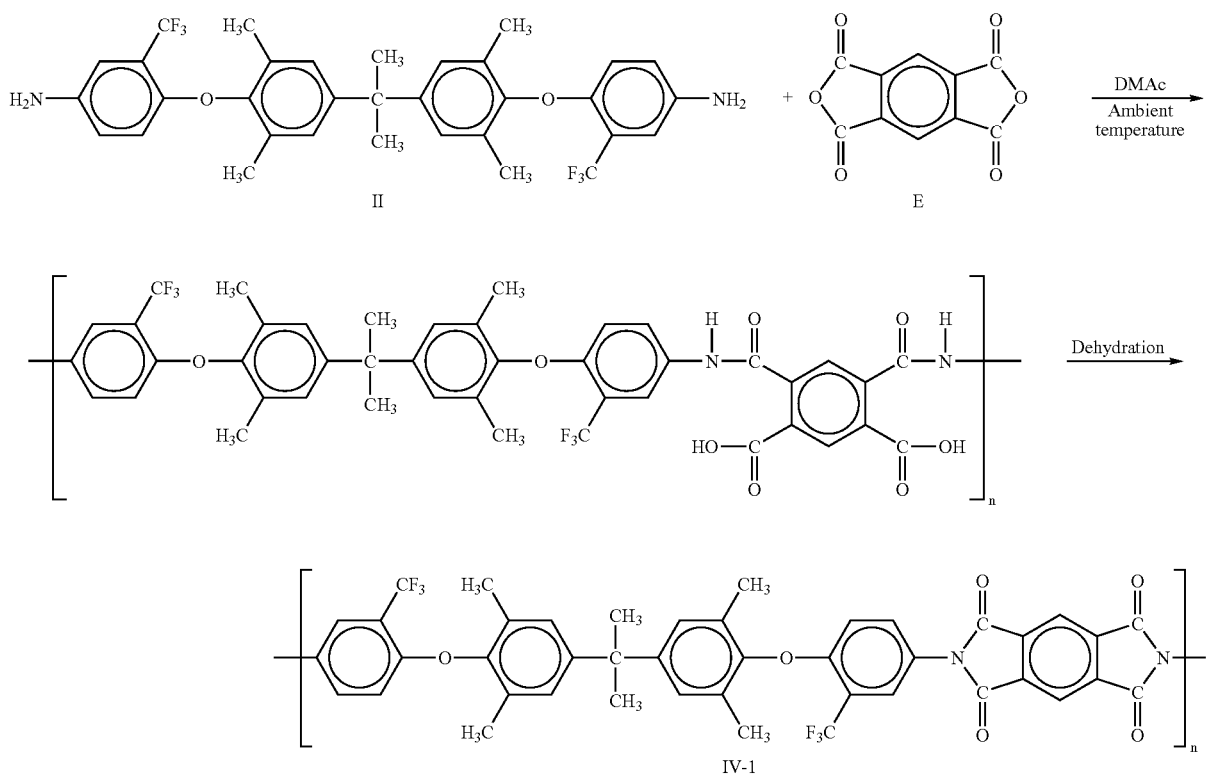

Embodiment VI

Synthesis of the Novel Polyimide Containing Flexible Isopropylidene, Trifluoromethyl and Tetramethyl Substituents from 2,2-bis[4-(2-trifluoromethyl-4-aminophenoxy)-3,5-dimethylphenyl]-propane and 333',4,4'-biphenyl Tetracarboxylic Dianhydride The reaction is performed by mixing a stirred solution of 1 mmol of 2,2-bis[4-(2-trifluoromethyl-4-aminophenoxy)-3,5-dimethyl -phenyl]propane (II) in 3.5 mL of N,N-dimethylacetamide (DMAc), 1 mmole of 3,3',4,4'-biphenyl tetracarboxylic dianhydride (F) were gradually added. The mixture is stirred at room temperature for 2-4 hrs under argon atmosphere to form the poly(amic acid). Chemical cyclodehydration is carried out by adding 0.6 mL of acetic anhydride and 0.6 mL of pyridine into the above-mentioned poly(amic acid) solution with stirring at room temperature for 1 hr, and then heating at 110° C. for 3 hrs. The polymer solution is poured into methanol. The precipitate is filtered, washed thoroughly with methanol and hot water, and dried at 100° C. under vacuum. The inherent viscosity of the polymer in N,N-dimethylacetamide (DMAc) is 0.82 dL·g$^{-1}$, measured at a concentration of 0.5 g·dL$^{-1}$ at 30° C. The IR spectrum (film) of the polyimide exhibits absorption bands at 1774 and 1711 cm$^{-1}$, which are attributed to the asymmetric and symmetric stretches of imide carbonyl groups, respectively. The C—N stretching absorption band at 1377 cm$^{-1}$ confirmed the formation of imide structure.

TABLE 4

Characterization of the polyimide containing flexible isopropylidene, trifluoromethyl and tetramethyl substituents in embodiment VI

| | |
|---|---|
| Molecular weight | Number average molecular weights: 5.7 × 10$^4$ |
| | PDI: 2.89 |
| | Number of repeating unit: 66 |
| Mechanical properties of thin film | Tensile strength: 92 MPa; |
| | Elongation at break: 8.5%; |
| | Tensile modulus: 2.2 GPa o |
| Solubility | The polymer can be dissolved in N-methyl-2-pyrrolidinone (NMP), N,N-dimethylacetamide (DMAc), N,N-dimethylformamide (DMF), chloroform, pyridine and tetrahydrofuran (THF), etc. |
| Thermal properties | Glass transition temperature: 270° C.; |
| | 10% weight loss temperature in the air: 433° C.; |
| | 10% weight loss temperature in the nitrogen: 456° C.. |
| Dielectric constant | 3.09 (1 KHz) |
| Optical properties | Wavelength of transmittance 80%: 448 nm |
| | Cut-off wavelength: 392 nm |
| Elemental analysis | Calculated value: C, 68.37%; H, 3.98%; N, 3.25% |
| | Observed value: C, 67.74%; H, 4.06%; N, 3.23% |

The reaction scheme is outlined as following:

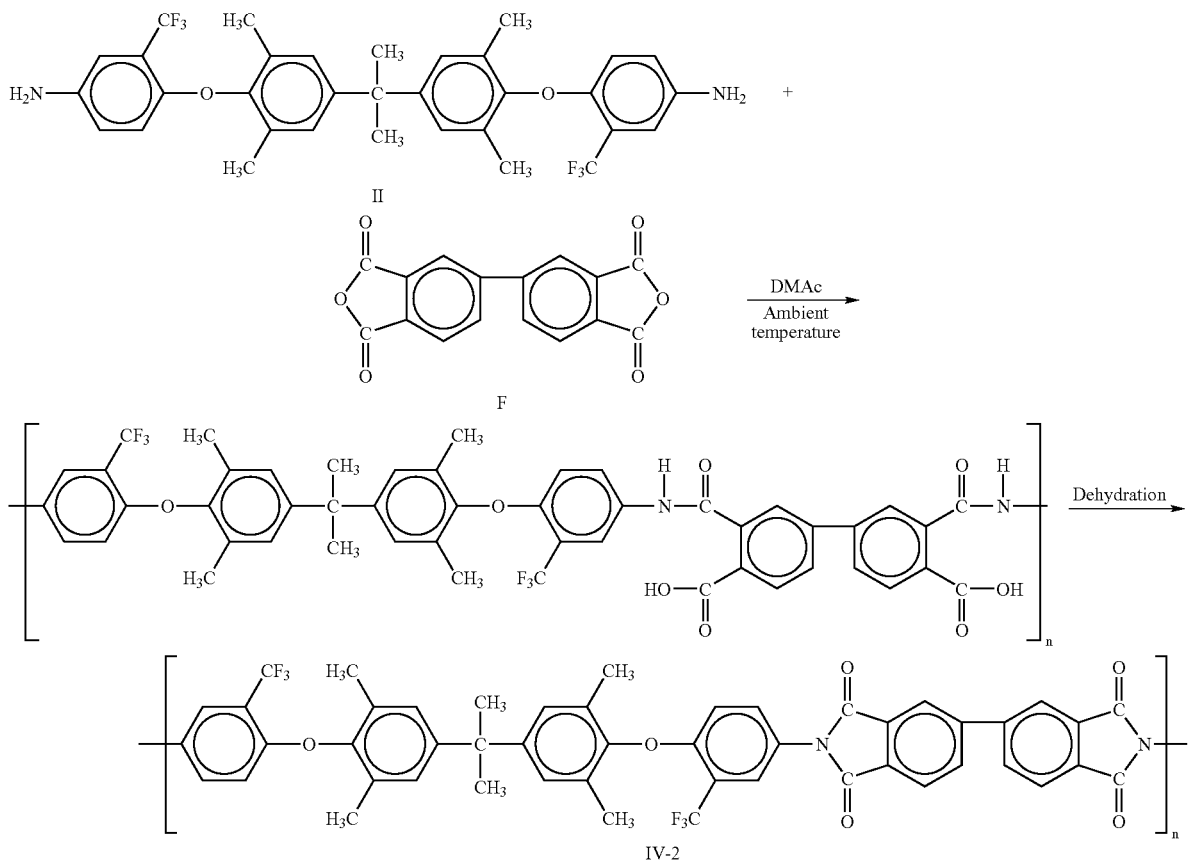

Embodiment VII

Synthesis of the Novel Polyimide Containing Flexible Isopropylidene Trifluoromethyl and Tetramethyl Substituents from 2,2-bis[4-(2-trifluoromethyl-4-aminophenoxy)-3,5-dimethylphenyl]-propane and 4,4'-oxydiphthalic Anhydride The reaction is performed by reacting a stirred solution of 1 mmol of 2,2-bis[4-(2-trifluoromethyl-4-aminophenoxy)-3,5-dimethylphenyl]propane (II) in 3.5 mL of N,N-dimethylacetamide (DMAc), 1 mmole of 4,4'-oxydiphthalic anhydride (G) were gradually added. The mixture is stirred at room temperature for 2-4 hrs under argon atmosphere to form the poly(amic acid). Chemical cyclodehydration is carried out by adding 0.6 mL of acetic anhydride and 0.6 mL of pyridine into the above-mentioned poly(amic acid) solution with stirring at room temperature for an hr, and then heating at 110° C. for 3 hrs. The polymer solution is poured into methanol. The precipitate is filtered, washed thoroughly with methanol and hot water, and dried at 100° C. under vacuum. The inherent viscosity of the polymer in N,N-dimethylacetamide (DMAc) is 0.80 dL·g$^{-1}$, measured at a concentration of 0.5 g·dL$^{-1}$ at 30° C. The IR spectrum (film) of the polyimide exhibits absorption band at 1780 and 1720 cm$^{-1}$, which are attributed to the asymmetric and symmetric stretches of imide carbonyl groups, respectively. The C—N stretching absorption band at 1374 cm$^{-1}$ confirmed the formation of imide structure.

TABLE 5

Characterization of the polyimide containing flexible isopropylidene, trifluoromethyl and tetramethyl substituents in embodiment VII

| | |
|---|---|
| Molecular weight | Number average molecular weights: 7.9 × 10$^4$<br>PDI: 1.52<br>Number of repeating unit: 90 |
| Mechanical properties of thin film | Tensile strength: 97 MPa;<br>Elongation at break: 15.5%;<br>Tensile modulus: 2.1 GPa |
| Solubility | The polymer can be dissolved in N-methyl-2-pyrrolidinone (NMP), N,N-dimethylacetamide (DMAc), N,N-dimethylformamide (DMF), chloroform, pyridine and tetrahydrofuran (THF), etc. |
| Thermal properties | Glass transition temperature: 258° C.;<br>10% weight loss temperature in the air: 458° C.;<br>10% weight loss temperature in the nitrogen: 421° C.. |
| Dielectric constant | 3.08 (1 KHz) |
| Optical properties | Wavelength of transmittance 80%: 432 nm<br>Cut-off wavelength: 362 nm |
| Elemental analysis | Calculated value: C, 67.12%; H, 3.91%; N, 3.19%<br>Observed value: C, 66.73%; H, 3.90%; N, 3.25% |

The reaction scheme is outlined as following:

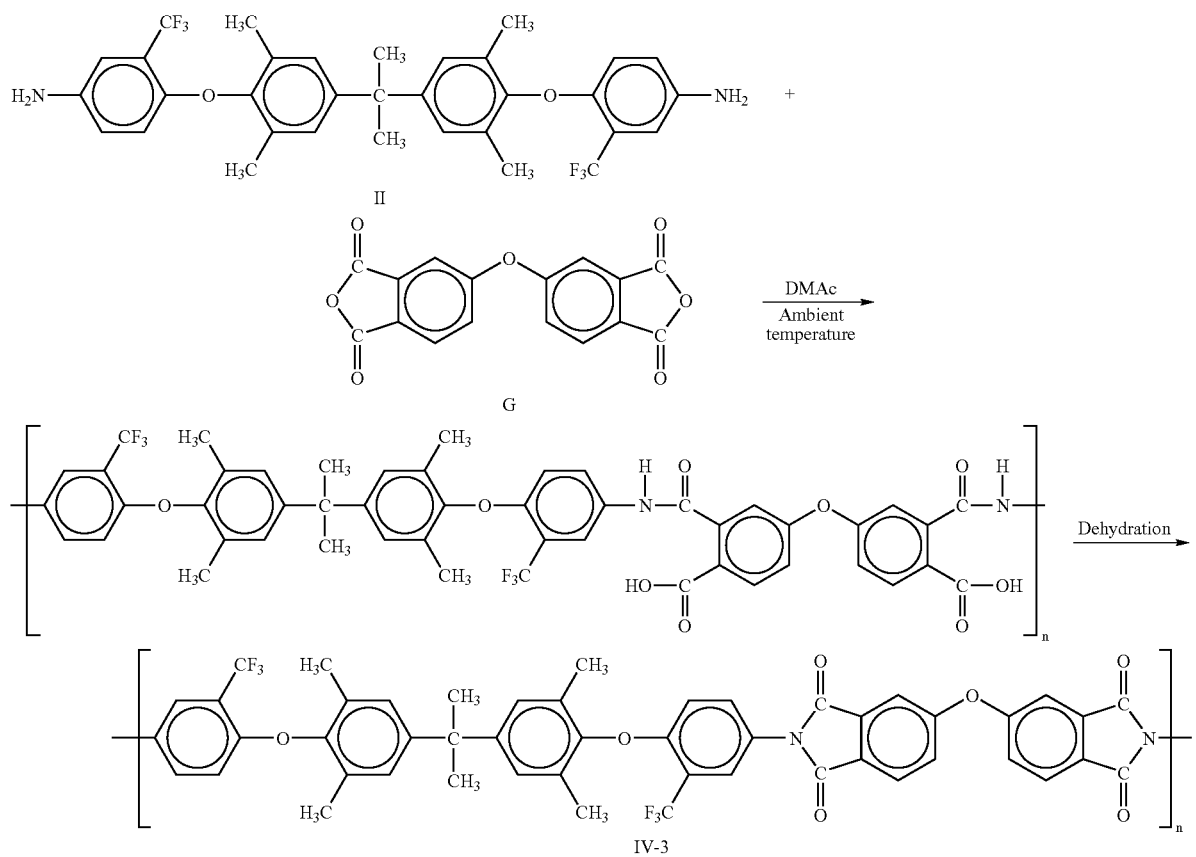

Embodiment VIII

Synthesis of the Novel Polyimide Containing Flexible Isopropylidene Trifluoromethyl and Tetramethyl Substituents from 2,2-bis [4-(2-trifluoromethyl-4-aminophenoxy)-3,5-dimethylphenyl]-propane and 3,3',4,4'-benzophenonetetracarboxylic Dianhydride The reaction is preformed by reacting a stirred solution of 1 mmol of 2,2-bis[4-(2-trifluoromethyl-4-aminophenoxy)-3,5-dimethylphenyl]propane (II) in 3.5 mL of N,N-dimethylacetamide (DMAc), 1 mmole of 3,3',4,4'-benzophenonetetracarboxylic dianhydride (H) were gradually added. The mixture is stirred at ambient temperature for 2-4 hrs under argon atmosphere to form the poly(amic acid). Chemical cyclodehydration is carried out by adding 0.6 mL of acetic anhydride and 0.6 mL of pyridine into the above-mentioned poly(amic acid) solution with stirring at room temperature for 1 hr, and then heating at 110° C. for 3 hrs. The polymer solution is poured into methanol. The precipitate is filtered, washed thoroughly with methanol and hot water, and dried at 100° C. under vacuum. The inherent viscosity of the polymer in N,N-dimethylacetamide (DMAc) is 0.97 d·Lg$^{-1}$, measured at a concentration of 0.5 g·dL$^{-1}$ at 30° C. The IR spectrum (film) of the polyimide exhibits absorption bands at 1782 and 1722 cm$^{-1}$, which are attributed to the asymmetric and symmetric stretches of imide carbonyl groups, respectively. The C—N stretching absorption band at 1372 cm$^{-1}$ confirmed the formation of imide structure

TABLE 6

Characterization of the polyimide containing flexible isopropylidene, trifluoromethyl and tetramethyl substituents in embodiment VIII

| | |
|---|---|
| Molecular weight | Number average molecular weights: 3.5 × 10$^4$ |
| | PDI: 2.27 |
| | Number of repeating unit: 39 |
| Mechanical properties of thin film | Tensile strength: 88 MPa; |
| | Elongation at break: 24.5%; |
| | Tensile modulus: 2.0 GPa o |
| Solubility | The polymer can be dissolved in N-methyl-2-pyrrolidinone (NMP), N,N-dimethylacetamide (DMAc), N,N-dimethylformamide (DMF), chloroform, pyridine and tetrahydrofuran (THF), etc. |
| Thermal properties | Glass transition temperature: 256° C.; |
| | 10% weight loss temperature in the air: 459° C.; |
| | 10% weight loss temperature in the nitrogen: 430° C.. |
| Dielectric constant | 3.07 (1 KHz) |
| Optical properties | Wavelength of transmittance 80%: 470 nm |
| | Cut-off wavelength: 388 nm |
| Elemental analysis | Calculated value: C, 67.57%; H, 3.86%; N, 3.15% |
| | Observed value: C, 67.10%; H, 3.48%; N, 2.80% |

The reaction scheme is outlined as following:

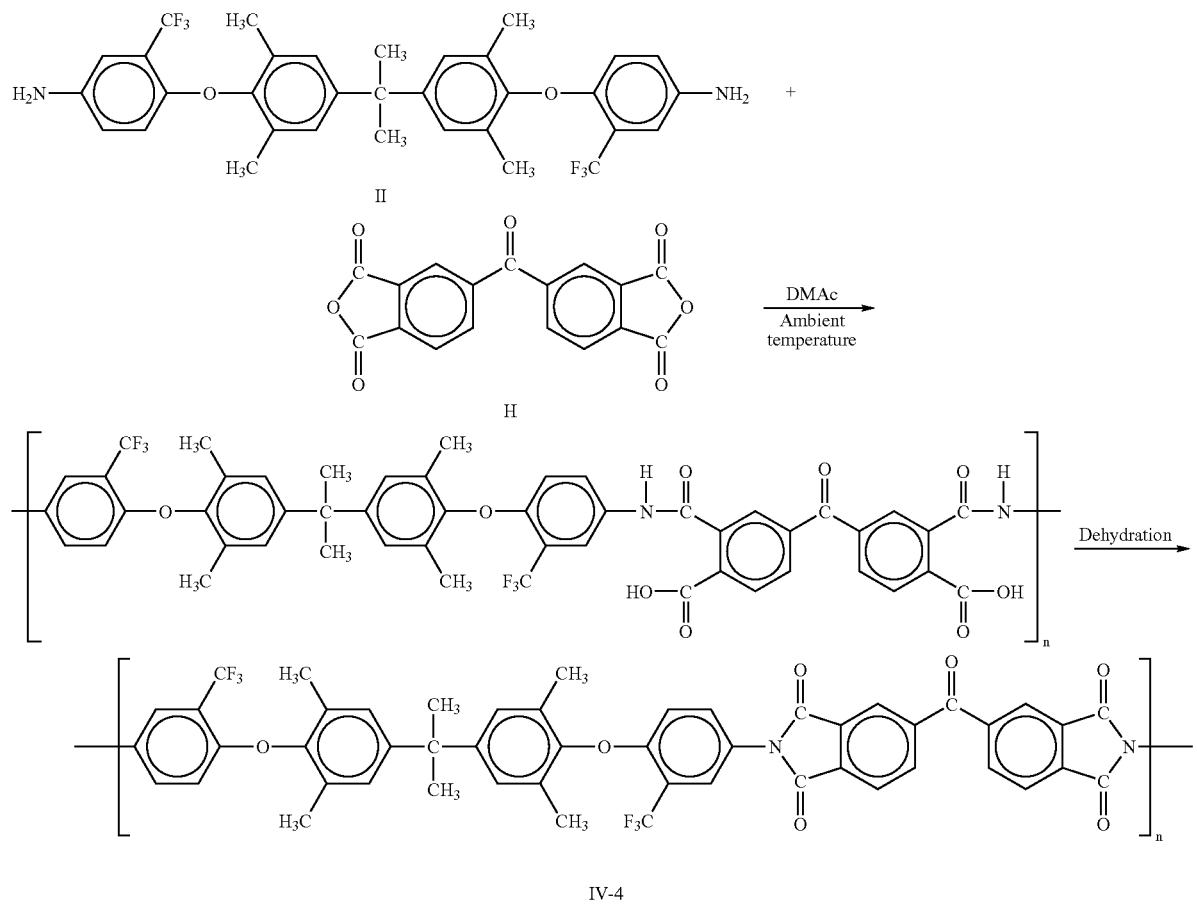

Embodiment IX

Synthesis of the Novel Polyimide Containing Flexible Isopropylidene Trifluoromethyl and Tetramethyl Substituents from 2,2-bis[4-(2-trifluoromethyl-4-aminophenoxy)-3,5-dimethylphenyl]-propane and 4,4'-sulfonyldiphthalic Anhydride The reaction is preformed by reacting a stirred solution of 1 mmol of 2,2-bis[4-(2-trifluoromethyl-4-aminophenoxy)-3,5-dimethylphenyl]propane (II) in 3.5 mL of N,N-dimethylacetamide (DMAc), 1 mmole of 4,4'-sulfonyldiphthalic anhydride (J) were gradually added. The mixture is stirred at ambient temperature for 2-4 hrs under argon atmosphere to form the poly(amic acid). Chemical cyclodehydration is carried out by adding 0.6 mL of acetic anhydride and 0.6 mL of pyridine into the above-mentioned poly(amic acid) solution with stirring at room temperature for 1 hr, and then heating at 110° C. for 3 hrs. The polymer solution is poured into methanol. The precipitate is filtered, washed thoroughly with methanol and hot water, and dried at 100° C. under vacuum. The inherent viscosity of the polymer in N,N-dimethylacetamide (DMAc) is 0.64 dL·g$^{-1}$, measured at a concentration of 0.5 g·dL$^{-1}$ at 30° C. The IR spectrum (film) of the polyimide exhibits absorption bands at 1783 and 1727 cm$^{-1}$, which are attributed to the asymmetric and symmetric stretches of imide carbonyl groups, respectively. The C—N stretching absorption band at 1378 cm$^{-1}$ confirmed the formation of imide structure

TABLE 7

Characterization of the polyimide containing flexible isopropylidene, trifluoromethyl and tetramethyl substituents in embodiment IX

| | |
|---|---|
| Molecular weight | Number average molecular weights: $2.1 \times 10^4$ |
| | PDI: 2.64 |
| | Number of repeating unit: 23 |
| Mechanical properties of thin film | Tensile strength: 83 Mpa; |
| | Elongation at break: 10.0%; |
| | Tensile modulus: 2.0 GPa o |
| Solubility | The polymer can be dissolved in N-methyl-2-pyrrolidinone (NMP), N,N-dimethylacetamide (DMAc), N,N-dimethylformamide (DMF), chloroform, pyridine and tetrahydrofuran (THF), etc. |
| Thermal properties | Glass transition temperature: 260° C.; |
| | 10% weight loss temperature in the air: 440° C.; |
| | 10% weight loss temperature in the nitrogen: 425° C.. |
| Dielectric constant | 3.07 (1 KHz) |
| Optical properties | Wavelength of transmittance 80%: 456 nm |
| | Cut-off wavelength: 374 nm |
| Elemental analysis | Calculated value: C, 63.64%; H, 3.71%; N, 3.03% |
| | Observed value: C, 62.55%; H, 3.67%: N, 2.98% |

The reaction scheme is outlined as following:

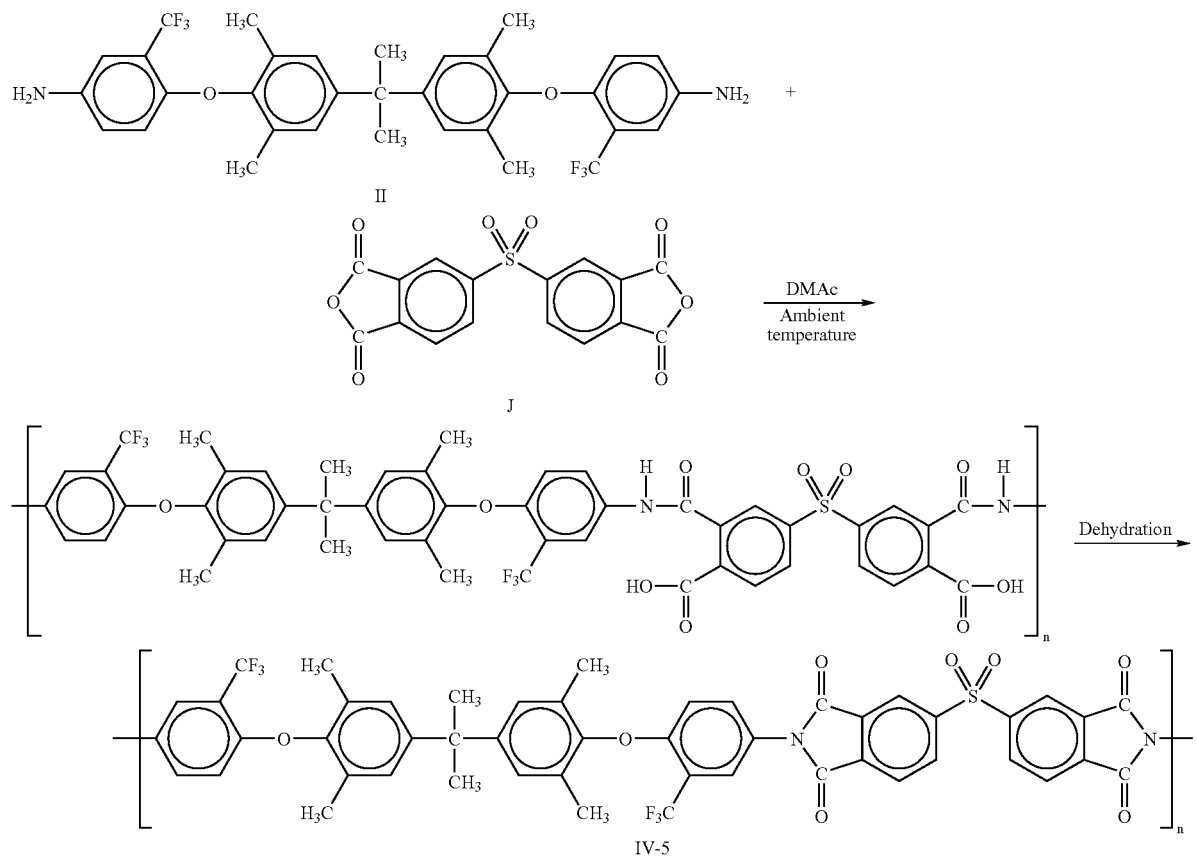

IV-5

Embodiment X

Synthesis of the Novel Polyimide Containing Flexible Isopropylidene, Trifluoromethyl and Tetramethyl Substituents from 2,2-bis[4-(2-trifluoromethyl-4-aminophenoxy)-3,5-dimethylphenyl]-propane and 4,4'-hexafluoroisopropylidenediphthalic Anhydride The reaction is preformed by reacting a stirred solution of 1 mmol of 2,2-bis[4-(2-trifluoromethyl-4-aminophenoxy)-3,5-dimethylphenyl]propane (II) in 3.5 mL of N,N-dimethylacetamide (DMAc), 1 mmole of 4,4'-hexafluoroisopropylidenediphthalic anhydride (K) were gradually added. The mixture is stirred at ambient temperature for 2-4 hrs under argon atmosphere to form the poly(amic acid). Chemical cyclodehydration is carried out by adding 0.6 mL of acetic anhydride and 0.6 mL of pyridine into the above-mentioned poly(amic acid) solution with stirring at ambient temperature for an hr, and then heating at 110° C. for 3 hrs. The polymer solution is poured into methanol. The precipitate is filtered, washed thoroughly with methanol and hot water, and dried at 100° C. under vacuum. The inherent viscosity of the polymer in N,N-dimethylacetamide (DMAc) is 0.70 dL·g$^{-1}$, measured at a concentration of 0.5 g·dL$^{-1}$ at 30° C. The IR spectrum (film) of the polyimide exhibits absorption bands at 1785 and 1726 cm$^{-1}$, which are attributed to the asymmetric and symmetric stretches of imide carbonyl groups, respectively. The C—N stretching absorption band at 1372 cm$^{-1}$ confirmed the formation of imide structure.

TABLE 8

Characterization of the polyimide containing flexible isopropylidene, trifluoromethyl and tetramethyl substituents in embodiment X

| | |
|---|---|
| Molecular weight | Number average molecular weights: 2.1 × 10$^4$ |
| | PDI: 2.64 |
| | Number of repeating unit: 21 |
| Mechanical properties of thin film | Tensile strength: 83 MPa; |
| | Elongation at break: 10.0%; |
| | Tensile modulus: 2.0 GPa |
| Solubility | The polymer can be dissolved in N-methyl-2-pyrrolidinone (NMP), N,N-dimethylacetamide (DMAc), N,N-dimethylformamide (DMF), chloroform, pyridine and tetrahydrofuran (THF), etc. |
| Thermal properties | Glass transition temperature: 264° C.; |
| | 10% weight loss temperature in the air: 462° C.; |
| | 10% weight loss temperature in the nitrogen: 443° C.. |
| Dielectric constant | 2.84 (1 KHz) |
| Optical properties | Wavelength of transmittance 80%: 440 nm |
| | Cut-off wavelength: 356 nm |
| Elemental analysis | Calculated value: C, 61.79%; H, 3.39%; N, 2.77% |
| | Observed value: C, 60.79%; H, 3.26%; N, 2.76% |

The reaction scheme is outlined as following:

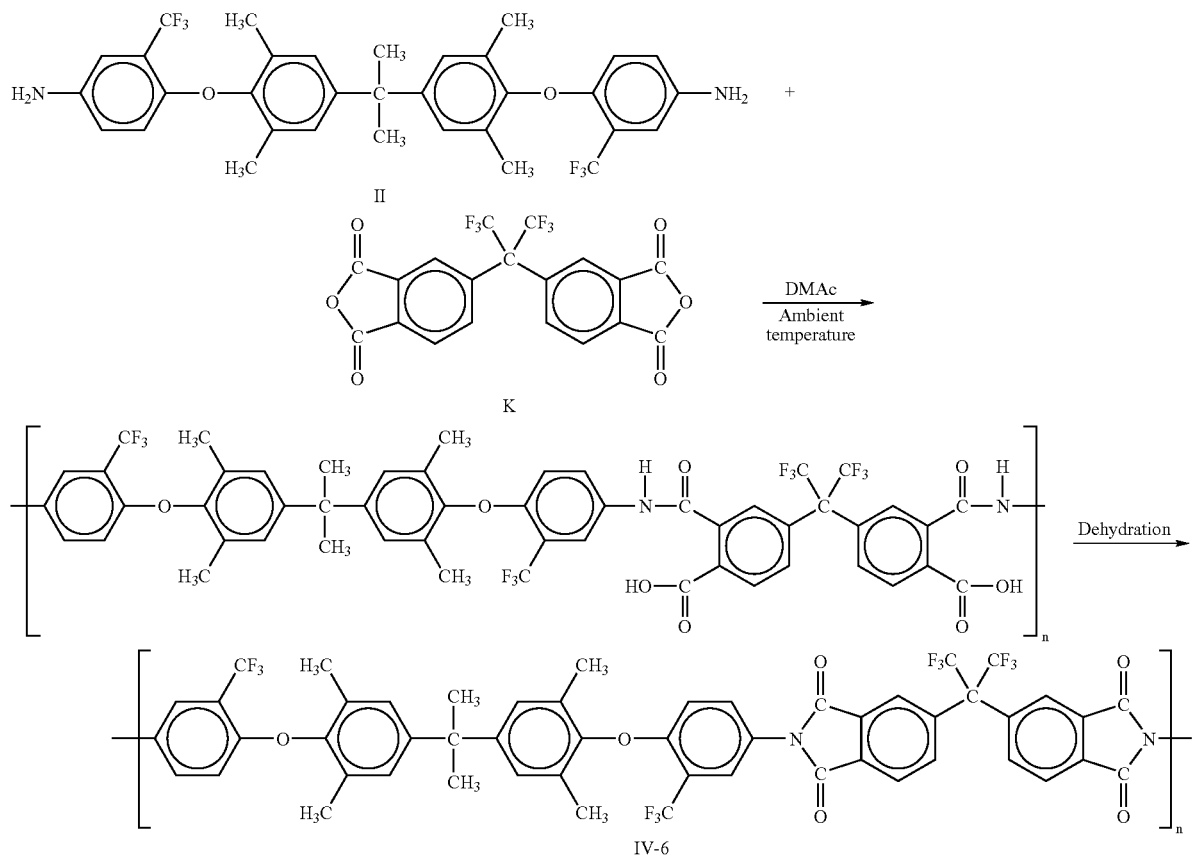

In conclusion, the present invention provides polyamide and polyimide containing flexible isopropylidene, trifluoromethyl and tetramethyl substituents and the preparing method thereof. The preparation method includes a polycondensation with a diamine compound containing flexible isopropylidene, trifluoromethyl and tetramethyl substituents and an equimolar diacid or a polycondensation with a diamine compound containing flexible isopropylidene, trifluoromethyl and tetramethyl substituents and an equimolar dianhydride. After polycondensation, the polyamide and polyimide containing flexible isopropylidene, trifluoromethyl and tetramethyl substituents are obtained. The polyamides and polyimides containing flexible isopropylidene, trifluoromethyl and tetramethyl substituents have excellent thermal stabilities, mechanical properties, processability so as to overcome the drawbacks of the prior engineering plastics.

While the invention has been described in terms of what is presently considered to be the most practical and preferred embodiments, it is to be understood that the invention needs not to be limited to the disclosed embodiment. On the contrary, it is intended to cover various modifications and similar arrangements included within the spirit and scope of the appended claims, which are to be accorded with the broadest interpretation so as to encompass all such modifications and similar structures.

What is claimed is:

1. A dinitro compound containing flexible isopropylidene, trifluoromethyl and tetramethyl substituents, comprising a chemical structure (I):

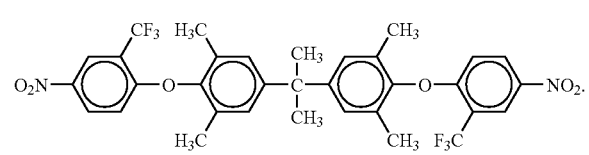

2. A diamine compound containing flexible isopropylidene, trifluoromethyl and tetramethyl substituents, comprising a chemical structure (II):

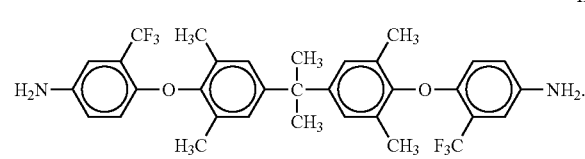

3. A polyamide containing flexible isopropylidene, trifluoromethyl and tetramethyl substituents, comprising a chemical structure (III):

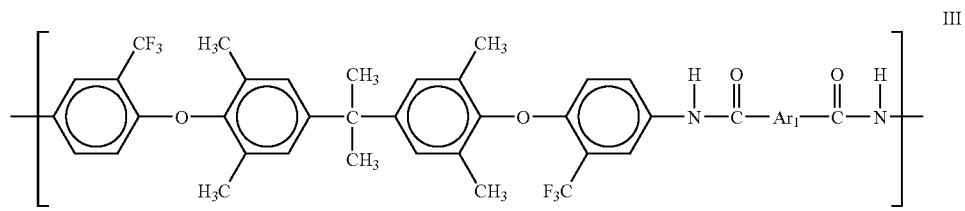

wherein Ar1 is one selected from a group consisting of:

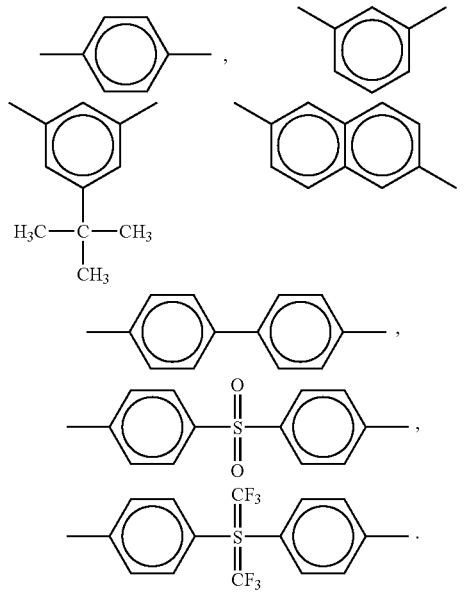

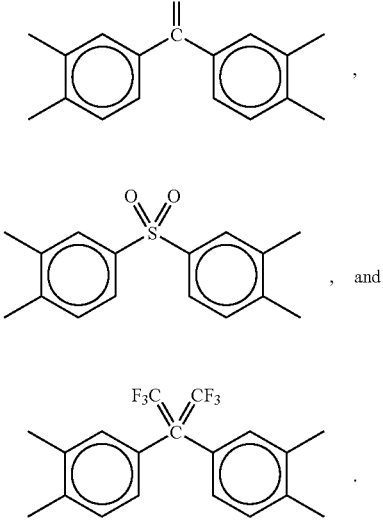

4. A polyimide containing flexible isopropylidene, trifluoromethyl and tetramethyl substituents, comprising a chemical structure (IV):

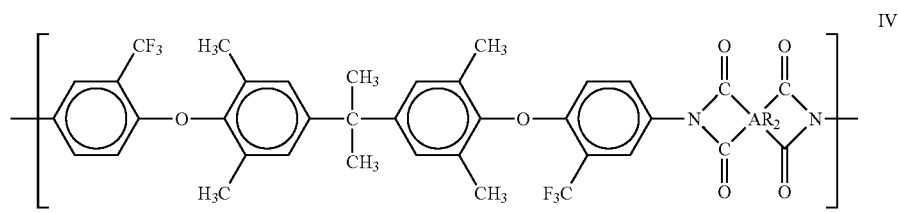

wherein Ar2 is one selected from a group consisting of:

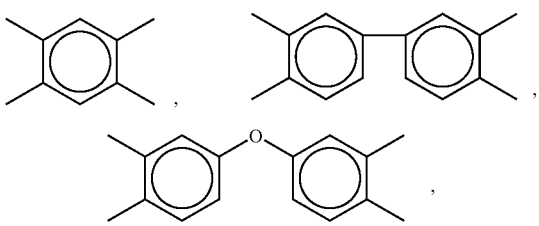

5. A method for preparing a dinitro compound containing flexible isopropylidene, trifluoromethyl and tetramethyl substituents (I) comprising: performing a reaction of 2,2-bis (4-hydroxy-3,5-dimethylphenyl)propane and 2-chloro-5-nitrobenzotrifluoride to obtain said compound (I):

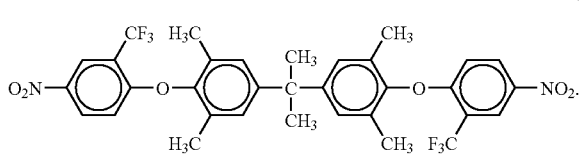

6. The method as claimed in claim 5, wherein N,N-dimethylformamide (DMF) is used as a solvent in said reaction.

7. The synthesis method as claimed in claim 5, further comprising using a mixture of water and methanol solution to obtain a precipitated compound.

8. The method as claimed in claim 7, wherein compound (I) is purified by recrystallization from glacial acetic acid.

9. A method for preparing a polyamide containing flexible isopropylidene, trifluoromethyl and tetramethyl substituents (III), comprising:

performing a reaction of said compound (II) according to claim 2 and an equimolar diacid to obtain the polyamide containing flexible isopropylidene, trifluoromethyl and tetramethyl substituents (III)

-continued

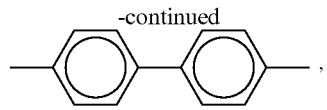

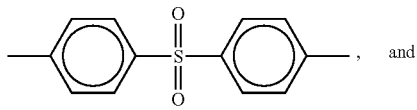, and

II

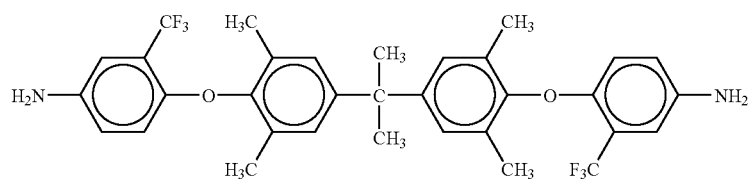

III

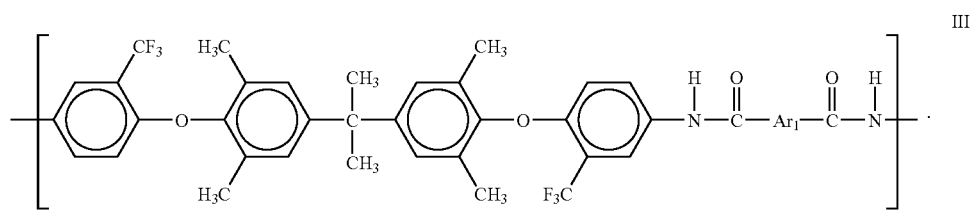

wherein Ar₁ is one selected from a group consisting of:

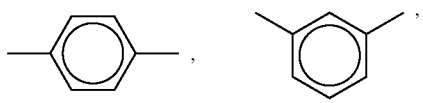,

-continued

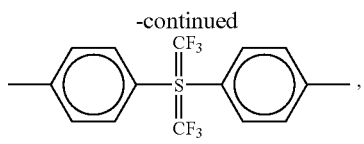,

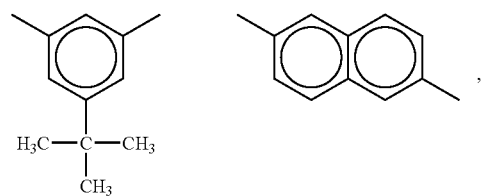,

10. The method as claimed in claim 9, wherein a solvent used in said reaction is one selected from a group consisting of calcium chloride (CaCl₂), triphenyl phosphate (TPP), pyridine, and N-methyl-2-pyrrolidinone (NMP).

11. A method for preparing a polyimide containing flexible isopropylidene, trifluoromethyl and tetramethyl substituents (IV), comprising:

performing a reaction of said compound (II) according to claim 2 and an equimolar dianhydride to obtain said polyimide containing flexible isopropylidene, trifluoromethyl and tetramethyl substituents (IV):

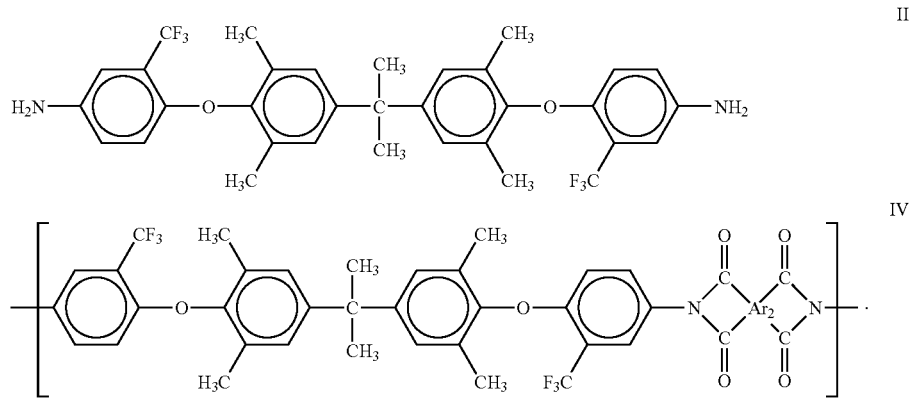

wherein Ar$_2$ is one selected from a group consisting of.

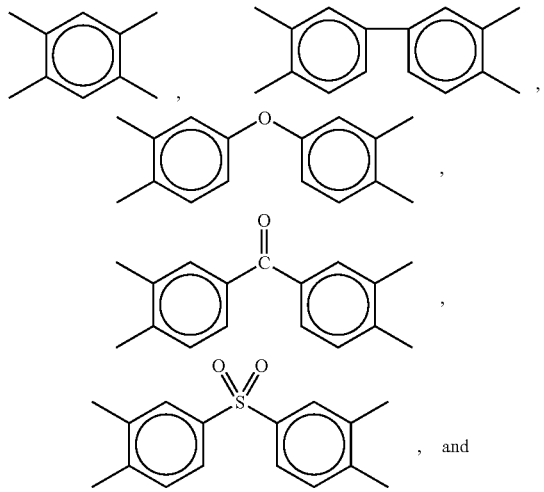

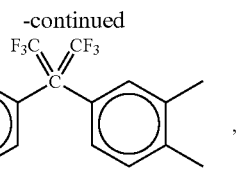

, and

-continued

12. The method as claimed in claim 11, wherein N,N-dimethylacetamide (DMAc) is used as a solvent in said reaction.

13. The method as claimed in claim 11, wherein a mixture of acetic anhydride and pyridine is added in said reaction, and said reaction is performed to obtain said polyimide containing flexible isopropylidene, trifluoromethyl and tetramethyl substituents (IV) at a refluxing temperature.

* * * * *

UNITED STATES PATENT AND TRADEMARK OFFICE
CERTIFICATE OF CORRECTION

PATENT NO. : 7,282,553 B2 Page 1 of 1
APPLICATION NO. : 10/883117
DATED : October 16, 2007
INVENTOR(S) : Der-Jang Liaw It is certified that error appears in the above-identified patent and that said Letters Patent is hereby corrected as shown below:

On the Title Page, Item (54), line 4, replace "FLUOROPOLYMIDE" with --FLUOROPOLYIMIDE--

Column 1, Line 4, replace "FLUOROPOLYMIDE" with --FLUOROPOLYIMIDE--

Signed and Sealed this

First Day of April, 2008

JON W. DUDAS
*Director of the United States Patent and Trademark Office*